(12) United States Patent
Waitzman et al.

(10) Patent No.: US 10,201,480 B2
(45) Date of Patent: Feb. 12, 2019

(54) FEEDING TUBE ASSEMBLY WITH A LIGHT ELEMENT ATTACHABLE THERETO

(71) Applicant: Cnicus, LLC, Riverwoods, IL (US)

(72) Inventors: Kathryn A. M. Waitzman, Riverwoods, IL (US); Bradley F. Slaker, Loretto, MN (US)

(73) Assignee: Cnicus, LLC, Riverwoods, IL (US)

( * ) Notice: Subject to any disclaimer, the term of this patent is extended or adjusted under 35 U.S.C. 154(b) by 0 days.

(21) Appl. No.: 14/847,039

(22) Filed: Sep. 8, 2015

(65) Prior Publication Data

US 2017/0065491 A1    Mar. 9, 2017

(51) Int. Cl.
*A61B 5/06* (2006.01)
*A61J 15/00* (2006.01)

(52) U.S. Cl.
CPC .......... *A61J 15/0003* (2013.01); *A61B 5/064* (2013.01); *A61J 15/0088* (2015.05)

(58) Field of Classification Search
CPC .......... A61B 5/06; A61B 5/0084; A61J 15/00; A61J 15/0003; A61J 15/0011; A61J 15/0026; A61J 15/0073; A61J 15/008; A61J 15/0084; A61J 15/0088
USPC ................. 600/424, 433, 434, 478
See application file for complete search history.

(56) References Cited

U.S. PATENT DOCUMENTS

| | | | | |
|---|---|---|---|---|
| 5,431,647 A | * | 7/1995 | Purcell, Jr. | A61B 18/24 606/15 |
| 2006/0104593 A1 | * | 5/2006 | Gowda | G02B 6/262 385/140 |
| 2008/0194973 A1 | * | 8/2008 | Imam | A61B 19/54 600/478 |
| 2008/0277926 A1 | * | 11/2008 | Inman, Jr. | A61M 39/10 285/123.15 |
| 2013/0046172 A1 | * | 2/2013 | Waitzman | A61B 5/06 600/424 |
| 2015/0112132 A1 | * | 4/2015 | Nieman | A61M 25/0147 600/109 |

OTHER PUBLICATIONS

MIT material property database (http://www.mit.edu/~6.777/matprops/pmma.htm, Jul. 17, 2004).*
Light, W. D., and F. M. Smolka. "Optical characteristics of a clear epoxy." Applied optics 17.22 (1978): 3518-3519.*
Merriam Webster Dictionary entry for "ferrule" (http://www.merriam-webster.com/dictionary/ferrule).*

* cited by examiner

*Primary Examiner* — Carolyn A Pehlke
(74) *Attorney, Agent, or Firm* — The Watson IP Group, PLC; Jovan N. Jovanovic; Vladan M. Vasiljevic

(57) ABSTRACT

A feeding tube assembly comprising a feeding tube body and an optical system. The feeding tube body includes an administration lumen and an optical lumen. The optical lumen is isolated relative to the administration lumen, with the distal end opening corresponding to the distal opening of the administration lumen. The optical system includes an optical element and an end dispersion element. The optical element is positioned within the optical lumen and the first end of the optical element is attachable to a fiber optic line. The end dispersion element is positioned at the second end of the optical element and is structurally configured to disperse light transmitted through the optical element.

17 Claims, 6 Drawing Sheets

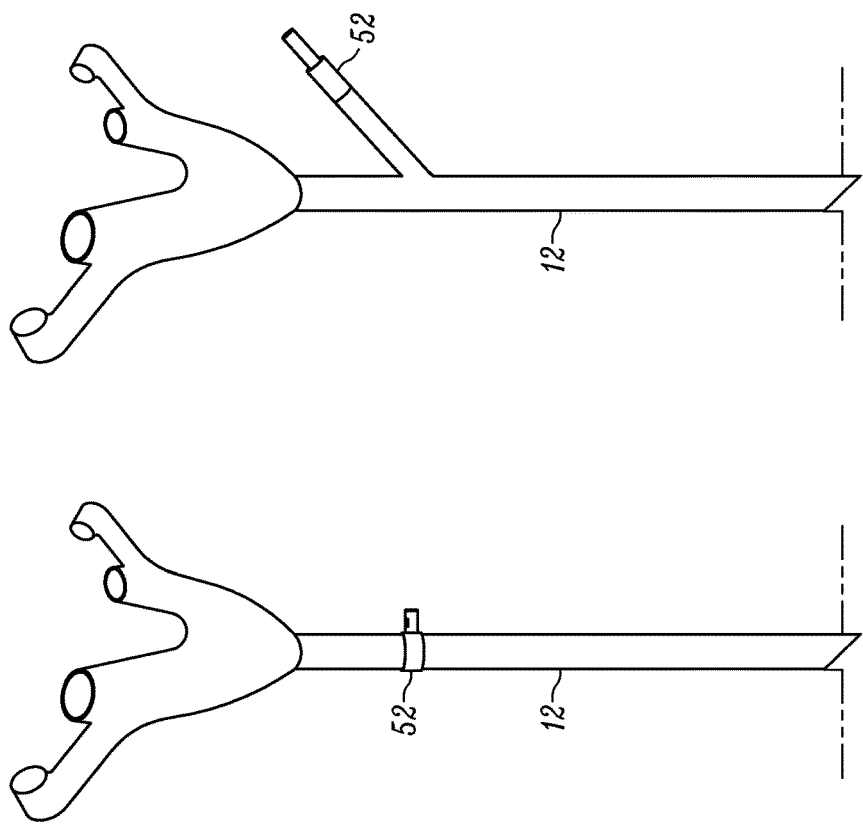
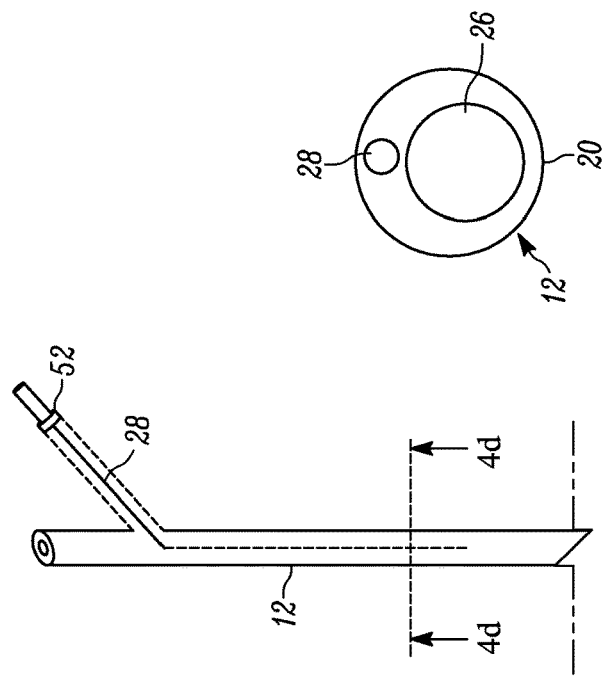
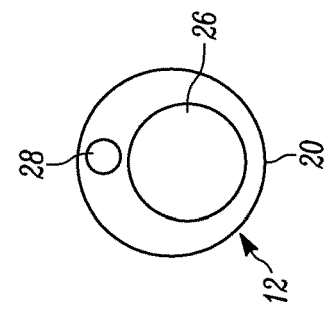
FIG. 4a  FIG. 4b  FIG. 4c  FIG. 4d

FEEDING TUBE ASSEMBLY WITH A LIGHT ELEMENT ATTACHABLE THERETO

CROSS-REFERENCE TO RELATED APPLICATION

N/A

BACKGROUND OF THE DISCLOSURE

1. Field of the Disclosure

The disclosure relates in general to techniques to confirm the location of a medical device in a medical patient's body, and more particularly, embodiments of the present disclosure relate to a feeding tube assembly and a light element which is attachable to the feeding tube assembly to identify and confirm that the end of a particular feeding tube that has been inserted into a patient without exposing the patient to radiation.

2. Background Art

Feeding tube intubation is a process involving placement of a soft plastic tube into a patient's stomach or jejunum, otherwise referred to as the small intestine. Typically, the gastric or intestinal feeding tube is inserted through a patient's nose or mouth and travels past the pharynx, down the esophagus and into a patient's stomach or beyond to the small intestine. Intubation is a common medical practice that may assist in the treatment and diagnosis of patients. For example, the intubation of a gastric feeding tube can aid a patient in recovery from surgery or trauma by administering life sustaining nutrition or medications where necessary. Patients who need gastric or intestinal feeding tubes include but are not exclusive to pre-mature neonates, comatose patients, patients requiring mechanical ventilation, chronically ill children, patients requiring face or neck surgeries, cancer patients, and/or post-op surgical nutrition. The feeding tubes are considered temporary, non-surgical, and intended to remain in use for short-term or long-term therapies until a trained physician deems a change medically necessary.

Gastric feeding tube placement is routinely practiced in both medical facilities and in the treatment of in-home-care patients. Intestinal feeding tube placement frequently requires the use of more specialized placement techniques and the placement position is more difficult to confirm in placement. As such, intestinal feeding tube placement is predominantly practiced only in medical facilities.

Feeding tubes are routinely placed in patients using a blind technique, with the operator not knowing the true location of the end of the tube after placement. Accordingly, the end of the feeding tube is commonly misplaced inside of the patient, which may lead to serious problems. For example, where a feeding tube intended for placement in the stomach is not placed deep enough, fluids administered through the feeding tube may seep into the lungs causing problems for the patient. Alternatively, where such a feeding tube is placed too deep, the fluids may be absorbed directly into the intestine, which may not have the appropriate enzymes for processing the fluids, which may also lead to problems. Complications that may result from the improper administration of fluids through an improperly placed feeding tube may include, but are not limited to, pneumothorax, perforated bowel, pneumonia, intestinal distention, aspiration, peritonitis, or placement of the tube into the brain, for example. See, Ellet, Maahs, and Forsee, Prevalence of Feeding Tube Placement Errors and Associated Risk Factors in children, American Journal Maternal Child Nursing, 23:234-39, published 1998; Ellet, What is Known About Methods Of Correctly Placing Gastric Tubes in Adults and Children, Gastroenterology Nursing, 27 (6):253-59, published 2004; Ellet, What is the Prevalence of Feeding Tube Placement Errors and What are the Associated Risk Factors?, The Online Journal of Knowledge Synthesis for Nursing, 4, document 5, published 1997.

The misplacement of feeding tubes in patients happens frequently when blind insertion techniques are used. Research has suggested that blind placement methods of feeding tubes may have a mal-position rate in pediatric and adult patients of up to 40%, moreover more than 20% of the misplaced nasogastric tubes led to pulmonary complications. See Irving, Northington, Kemper Nasogastric Tube Placement and Verification in Children: Review of Current Literature, Nutrition in Clinical Practice, Vol. XX, No. X, published 2014; Metheny and Tiller Assessing Placement of Feeding Tubes, American Journal of Nursing, 101:36-41, published 2001; Metheney and Meert, Monitoring Feeding Tube Placement, Nutrition in Clinical Practice, Vol. 19, no. 5, pp. 487-95, published 2004; Huffman, Karczk, O'Brien, Pieper and Bayne, Methods to Confirm Feeding Tube Placement: Application of Research in Practice, Pediatric Nursing, 30:10-13, published 2004; Westhaus, Methods to Test Feeding Tube Placement in Children, The American Journal of Maternal/Child Nursing, 29:282-87, published 2004; Ellet, How Accurate is Enteral Tube Placement in Children?, MNRS Connection, 14 (1), 14, published 1998. Accordingly, it is often necessary to confirm the location of the feeding tube prior to the administration of any medication or nutrition to avoid problems caused by feeding tube misplacement.

Conventional methods for locating the position of a feeding tube or tubes inside a patient include the use of air insufflation, gastric pH detection methods, gastric enzyme detectors and $CO_2$ detectors. There are problems, however, with the accuracy and reliability of these methods. See Gharpure, Meert, Sarnaik and Metheny, Indicators of Postpyloric Feeding Tube Placement in Children, Critical Care Medicine, 28:2962-66, published 2000; Metheny, Stewart, Smith, Yan, Diebold and Clouse, pH and Concentration of Bilirubin in Feeding Tube Aspirates as Predictors of Tube Placement, Nursing Research 48, 189-97, published 1999; Araujo-Preza, Melhado, Gutierrez, Maniatis and Castellano, Use of Capnometry to Verify Feeding Tube Placement, Critical Care Medicine, 30:2255-2259, published 2002. For example, air insufflation techniques require a user to confirm the location of a tube by listening for a sound of air passing through a feeding tube inside the patient using a stethoscope. Internal noises may lead to a false confirmation of proper placement, for example. Furthermore, feedings and medications may affect the levels of pH, enzyme and $CO_2$ in a patient, thereby affecting the ability of gastric pH, gastric enzymes, and $CO_2$ detectors to produce accurate and reliable results.

Moreover, conventional methods typically require the implementation of equipment that is only available in a hospital or clinical setting and are thus unavailable for use with in-home-care patients. Presently, only air insufflation, the least accurate of the methods, is available to confirm proper placement of feeding tubes for in-home-care patients.

In June 2005, the American Association of Critical-Care Nurses (AACN) issued a practice alert. The alert recommended using an X-ray to visualize a new, blindly inserted gastric tube to ensure that the tube has been properly placed and is in the desired position of the stomach or small intestine before initiating the administration of formula or medications via the tube. See American Association of Critical Care Nurses, Practice Alert-Verification of Feeding Tube Placement, May 2005. Though more accurate than the conventional methods described above, the use of such techniques typically requires at least 5 X-ray scans to confirm the location of the tube, for each time an intestinal feeding tube is inserted blindly at a patients hospital bedside. It is not uncommon for children and neurologically compromised patients to personally remove/extubate the OG or NG tubes more than one time daily which would require additional X-rays for each new tube placement. Such persistent exposure to X-rays throughout a patient's treatment gives rise to serious concern, as the high levels of radiation can have harmful effects on the patient. This concern is especially great where the patient is a child. An additional disadvantage for using X-ray techniques to confirm feeding tube placement is that the equipment necessary to perform the techniques is typically only available in hospital environments and thus of no help to in-home-care patients.

Recently, the use of electromagnetic tube placement devices has provided a means to increase the accuracy of feeding tube placement without the need for X-ray exposure to patients. An example of such a device is the CORTRAK™ system produced by Cardinal Health. The electromagnetic systems involve the placement of an electromagnetic transmitter inside of the feeding tube. As the tube is inserted into the patient, an electromagnetic tracking device tracks the position of the feeding tube, and displays the location on a display unit. Accordingly, operators can respond immediately where a tube placement does not follow the expected path. Because these techniques are only available in medical facilities, they are not helpful when needed for in-home-care.

Once the feeding tube has been inserted into the patient using the aforementioned electromagnetic tracking techniques, the transmitter device must be removed before feedings or medications can be administered through the tube. After the transmitter has been removed, and liquid nutrition started the transmitter must be reinserted into the feeding tube like a rigid stylet to reconfirm the location of the tube. This procedure must allow time lost to stop the administration of feedings to flush the lumen before transmitter reinsertion and adds the risk of tube perforation. Accordingly, once the transmitter has been removed, the position of a feeding tube inside the patient may not be checked. This shortcoming of the electromagnetic system is significant, as patient movement, periodic adjustment of the equipment, peristalsis and other internal functions all contribute to constant shifting and relocation of the feeding tube. Thus, it is necessary to periodically confirm the position of a feeding tube, even after it has been inserted. Without the transmitter located in the tube, the electromagnetic tracking techniques cannot confirm the position after insertion without the use of X-rays.

Thus, the concerns with the present feeding tube placement practices and techniques include several problems relating to accuracy, safety and ease of use for in-home-care patients. Thus a need exists for a method and/or system for detecting, and periodically re-checking, the location of a placed feeding tube in a patient's stomach or small intestine that has the accuracy of X-ray detection without the radiation exposure.

SUMMARY OF THE DISCLOSURE

The disclosure is directed to a feeding tube assembly. The feeding tube assembly includes a feeding tube body and an optical system. The feeding tube body has an administration lumen and an optical lumen. The administration lumen has a proximal opening end and a distal opening. The optical lumen has a proximal end opening and a distal end opening. The optical lumen is isolated relative to the administration lumen, with the distal end opening corresponding to the distal opening of the administration lumen. The optical system includes an optical element and a ferrule connector. The optical element has a first end and a second end and is positioned within the optical lumen. The first end thereof corresponds to the proximal end opening, and the second end corresponds to the distal end opening of the optical lumen. The ferrule connector is positioned proximate the proximal end opening of the optical lumen, and has a tip end extending therefrom. The first end of the optical element extends into the tip end. The tip end is structurally configured to be attachable to a fiber optic line. The end dispersion element is positioned at the second end of the optical element. The end dispersion element is structurally configured to disperse light transmitted through the optical element.

In some configurations, the ferrule connector extends about an outside surface of the feeding tube body. In some configurations, wherein the tip end extends substantially perpendicular to the outside surface of the feeding tube body.

In some configurations, the end dispersion element further comprises a hemispherical member having the second end of the optical element being embedded therein.

In some configurations, the hemispherical member has an index of refraction that is greater than an index of refraction of the optical element.

In some such configurations, the end dispersion element further includes an epoxy with reflectors embedded therein.

In some such configurations, the reflectors comprise titanium dioxide particles.

In some configurations, the end dispersion element further comprises the placement of the second end of the optical element within a second optical element, with an air pocket between a portion of the second end of the optical element and the second optical element.

In some such configurations, the second optical element is embedded within a hemispherical dispersion element.

In some configurations, the dispersion element further comprises a shaped second end of the optical element.

In some configurations, the feeding tube assembly further comprises an administration port assembly coupled to the proximal opening end of the administration lumen.

In some configurations, the feeding tube assembly further comprise at least one intermediate opening along the optical lumen with the optical element being visible therethrough.

In some configurations, the at least one intermediate dispersion element is positioned over the opening along the at least one intermediate opening.

In some configurations, the at least one intermediate dispersion element comprises a hemispherical dispersion element having an index of refraction that is greater than an index of refraction of the optical element.

In some configurations, a light element is coupled to the feeding tube assembly disclosed herein. The lighting element comprises a housing and a light emitting assembly. The light emitting assembly comprises a light source and a connector. The light source is positioned within the housing. The connector extends from the housing. The connector is structurally configured for coupling to a fiber optic line which is also attachable to the optical system.

In another aspect of the disclosure, the disclosure is directed to a feeding tube assembly. The feeding tube assembly includes a feeding tube body and an optical system. The feeding tube body has an administration lumen having a proximal opening end and a distal opening, and, an optical lumen having a proximal end and a distal end opening. The optical lumen is isolated relative to the administration lumen. The distal end opening corresponds to the distal opening of the administration lumen. The optical system includes an optical element and an end dispersion element. The optical element has a first end and a second end. The optical element is positioned within the optical lumen, with the first end corresponding to the proximal end opening, and the second end corresponding to the distal end opening of the optical lumen. The first end of the optical element is attachable to a fiber optic line. The end dispersion element is positioned at the second end of the optical element. The end dispersion element is structurally configured to disperse light transmitted through the optical element.

In some configurations, the feeding tube assembly further includes at least one intermediate opening along the optical lumen with the optical element being visible therethrough.

In some such configurations, the feeding tube assembly comprises at least one intermediate dispersion element positioned over the opening along the at least one intermediate opening.

In some such configurations, the at least one intermediate dispersion element comprises a hemispherical dispersion element having an index of refraction that is greater than an index of refraction of the optical element.

In some such configurations, the end dispersion element further comprises a hemispherical member having the second end of the optical element being embedded therein.

BRIEF DESCRIPTION OF THE DRAWINGS

The disclosure will now be described with reference to the drawings wherein:

FIGS. 4a through 4c of the drawings are each a side elevational view of different configurations of the feeding tube assembly of the present disclosure;

FIG. 4d of the drawings are a cross-sectional view of the feeding tube body of the present disclosure, showing, taken generally about lines 4-4 of FIG. 4c

DETAILED DESCRIPTION OF THE DISCLOSURE

Figure 1:
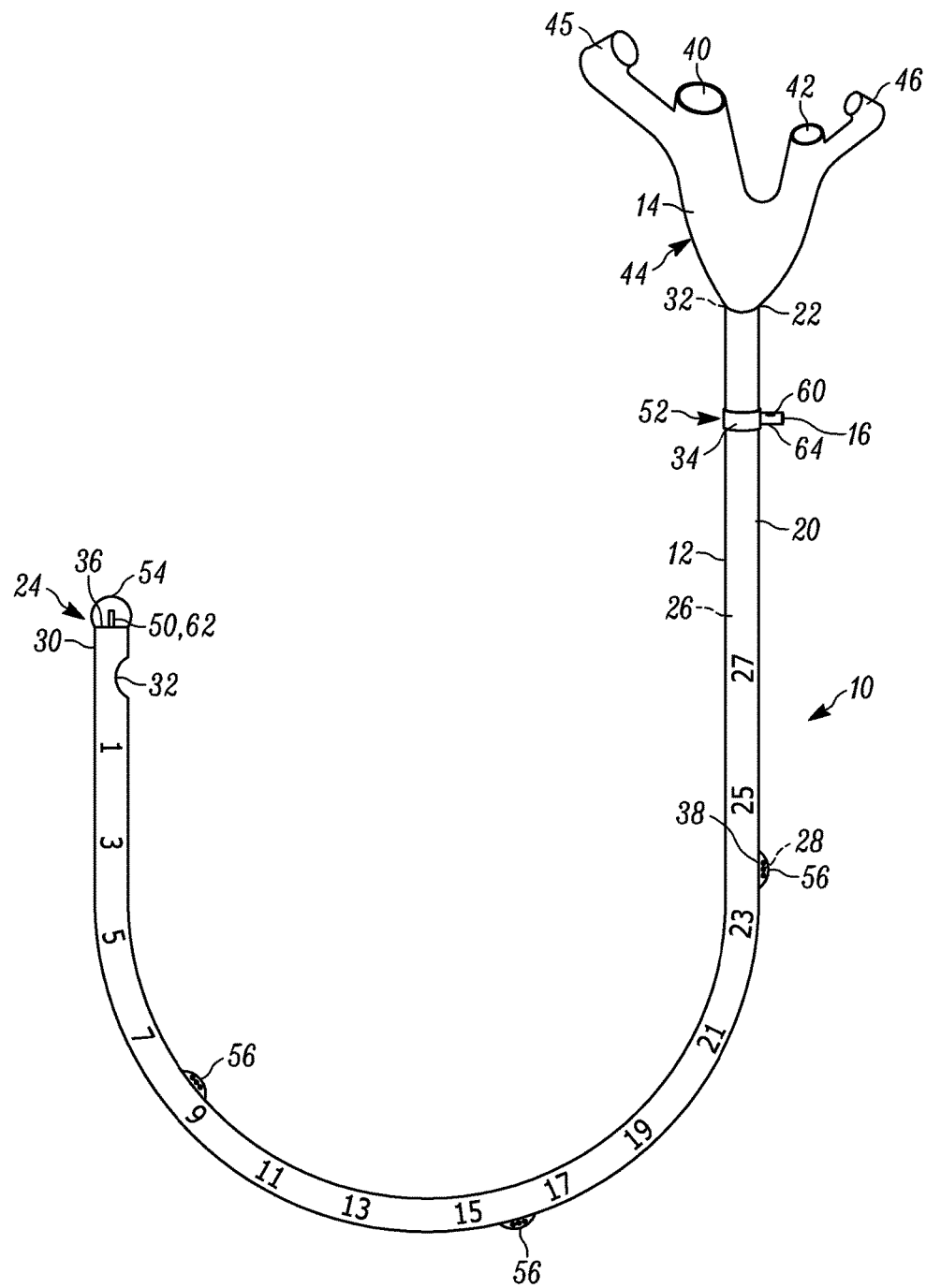
FIG. 1 of the drawings is a side elevational view of the feeding tube assembly of the present disclosure.

While this invention is susceptible of embodiment in many different forms, there is shown in the drawings and described herein in detail a specific embodiment with the understanding that the present disclosure is to be considered as an exemplification and is not intended to be limited to the embodiment illustrated.

It will be understood that like or analogous elements and/or components, referred to herein, may be identified throughout the drawings by like reference characters. In addition, it will be understood that the drawings are merely schematic representations of the invention, and some of the components may have been distorted from actual scale for purposes of pictorial clarity.

Referring now to the drawings and in particular to FIG. 1, the disclosure is directed to a feeding tube assembly 10 which is attachable to a light emitting element 100 (FIG. 2a) to assist with proper placement of the feeding tube assembly. As will be disclosed below, the lighting element is attachable to the feeding tube assembly so as to direct light to an output at the end of the feeding tube assembly and along the length thereof so as to provide visual feedback when the feeding tube assembly is inserted into a patient. The patient for which the present disclosure is a newborn or an infant, such as one that may be in a neonatal unit of a hospital. Of course, the disclosure is not limited to a patient of a particular age, although the aforementioned use is of particular interest.

The feeding tube assembly 10 is shown in FIG. 1 as comprising feeding tube body 12, administration port assembly 14 and optical system 16. The feeding tube body, preferably has an elongated, substantially cylindrical configuration. For example, the feeding tube body generally comprises a polyurethane tube having a size of, for example, a French gauge 6. Such a configuration has a diameter of 2 mm. It is contemplated that the feeding tube comprises a clear radiopaque polyurethane that is both x-ray visible and optically transparent. The feeding tube body has an outer surface 20 and extends from a proximal end 22 to a distal end 24. Markings may be positioned along the outer surface to indicate the distance from the distal end, for example, in millimeters or the like. Other markings or indicia are also positionable along the outer surface 20 of the feeding tube body, such as a correlation with age relations, height based measurements (ARHB measurements).

In the configuration shown, the feeding tube body includes an administration lumen 26 and an optical lumen 28 (with various configurations thereof shown in FIGS. 4d, and, 5a through 5d). The administration lumen 26 includes proximal opening end 30 and distal opening 32. The proximal opening end 30 coincides, in the configuration shown, with the proximal end 22 of the feeding tube body. The distal opening 32 is spaced apart from the distal end 24 of the feeding tube body, and extends out a side of the feeding tube body so as to be generally perpendicular to the administrative lumen. It will be understood that multiple distal openings 32 that are spaced apart along the outer surface of the feeding tube body may be disposed.

The optical lumen includes proximal end opening 34, distal end opening 36 and intermediate openings 38. The proximal end opening 34 is positioned at or near the proximal end of the feeding tube body 12. The distal end opening is positioned, preferably, at the distal end of the feeding tube body. The intermediate openings are disposed along the feeding tube body at strategic locations. In the configuration shown, a total of three intermediate openings are dispersed along the feeding tube body (at, for example 8 mm, 16 mm and 24 mm). Of course, the total number of intermediate openings, and the special position thereof can be varied without departing from the scope of the disclosure. And the configuration shown is merely for illustrative purposes, and should not be deemed as limiting.

In the configuration shown, the optical lumen has a diameter of approximately 0.5 mm, while other configurations are contemplated. In other configurations, the optical lumen may be either of a smaller or larger diameter. It is further contemplated that multiple optical lumen may be utilized with each lumen being of the same or different size. For example, different lumen may be utilized depending on the light source or depending on the patient. The disclosure is not limited to a single lumen, or a lumen of any particular diameter. The optical lumen is of a different side than the administration lumen. It will be understood that the optical lumen and the administration lumen are separated and typically are not in fluid communication with each other, so as to isolate one relative to the other. Such a separation precludes degradation of the elements from the instilled liquids, and allows for connection and disconnection of the optical element from a light source as desired without adversely affecting the flow of material through the administration lumen. The optical element 50 is non-removable.

The administration port assembly 14 is shown in FIG. 1 as comprising first administration port 40, second administration port 42 and adapter outlet 44. The first and second administration ports 40 are coupled together at the adapter outlet 44. A cap, such as cap 45 and 46 may be positionable over each of the first and second administration ports. Additionally, the adapter outlet 44 is coupled to the proximal opening end 30 of the administration lumen in sealed engagement. The administration port assembly provides the ability to couple devices in fluid communication with the administration lumen; in the configuration shown, two separate ports are provided (which may be coupled to two different sources). In other configurations, a single administration port may be provided, whereas in still other configurations, more than two administration ports may be provided.

The optical system 16 is shown in FIG. 1 as comprising optical element 50, ferrule connector 52, end dispersion element 54 and intermediate dispersion element 56 (with additional disclosure in FIGS. 3a through 3d, 4a through 4c and 6a through 6b). The optical element 50 comprises a plastic optical fiber (or a glass optical fiber) that includes first end 60 and second end 62. In the configuration shown, the optical element 50 extends through the optical lumen 28 with the first end 60 corresponding to the proximal end opening 34 of the optical lumen, and the second end 62 corresponding to the distal end opening 36 of the optical lumen. Additionally, the optical element is visible at each of the intermediate openings 38 positioned along the optical lumen and extending through the outer surface 20 of the feeding tube body 12. It will be understood that light passing through the optical element positioned therewithin is visible through the intermediate openings.

It will be understood that in certain configurations, multiple optical elements may be utilized, with a single optical element being positioned in each optical lumen, or with multiple elements positioned within a single optical lumen. The disclosure will be described with a single optical element within a single optical lumen, with the understanding that such other configurations are within the scope of the disclosure.

The ferrule connector 52 extends about the feeding tube body at the proximal end opening 34 of the optical lumen. The ferrule connector couples to the first end 60 of the optical element 50 and includes a tip end 64 which is coupled thereto. The ferrule connector provides strength and locates the first end 60 within the tip end 64 so as to provide a means by which to attach to the light element 100. For example, the tip end may comprise a fiber optic type connector, of, for example, the type LC, ST, MU or SC. In a configuration having multiple optical elements, multiple tip ends, such as tip end 64 may be provided. In other configurations, a single tip end 64 may include multiple optical elements. Additionally, in the configuration shown, the tip end 64 extends substantially perpendicular to the outer surface 20 of the feeding tube body 12.

In the configuration shown, the ferrule connector 52 extends about the outer surface 20 of the feeding tube body 12. In other configurations, the optical lumen 28 may branch off from the administration lumen 26 in a "y" configuration or the like (See, i.e., FIG. 4c). In such a configuration, the ferrule connector 52 extends about the optical lumen 28, with the tip end 64 extending parallel or co-axial with the lumen. An extension lumen or pigtail can connect the connection assembly 10 to the light source 100. In other configurations, the light source or the feeding tube assembly may have an extension lumen or a pigtail extending therefrom so that a separate pigtail or separate fiber optic cable may not be needed.

Referring again to FIG. 1, the end dispersion element comprises a dome like configuration which is intended to disperse any light travelling through the second end 62 of the optical element. In the configuration shown, and with further reference to FIG. 3a, the end dispersion element comprises an optically clear epoxy coupled to the end of the optical element in, for example, a hemispherical or dome like configuration 71. In the configuration shown, a titanium dioxide powder is mixed into the epoxy, with the epoxy having an index of refraction that is greater than that of the optical element.

In the configuration shown, and solely for illustrative purposes, the epoxy has an index of refraction that is greater than 1.50 with the optical element having an index of refraction that is approximately 1.49. Additionally, in a predetermined ratio, preferably, a titanium dioxide having a primary particle size of 200-250 nm is mixed into the epoxy. In such a configuration, the titanium dioxide powder functions much like a miniature reflector with random placement and orientation. Such a configuration leads to a generally uniform dispersion of optical energy in the hemispherical or dome like shape. Additionally, the second end 62 of the optical element is protected by the epoxy.

Figure 3A:
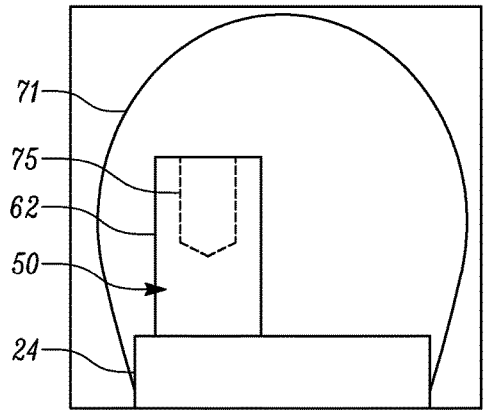
FIGS. 3a through 3d of the drawings are each a side elevational view of different configurations of the end dispersion elements of the optical system of the present disclosure.
Figure 3B:
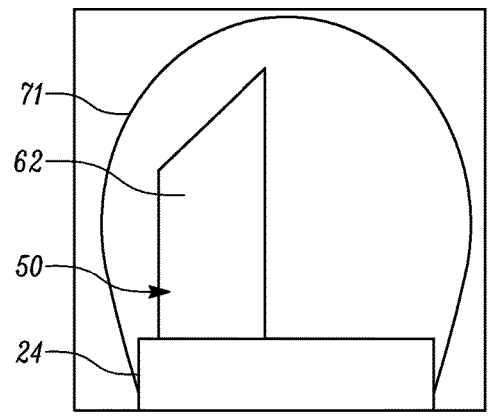
Figure 3C:
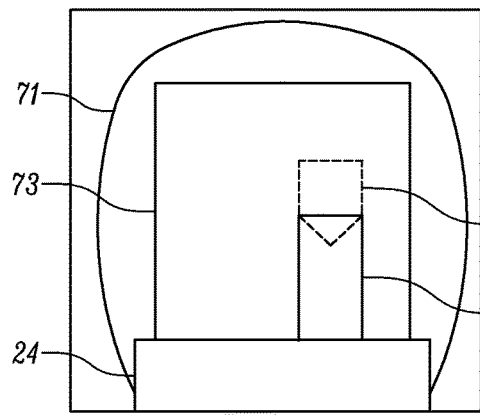
Figure 3D:
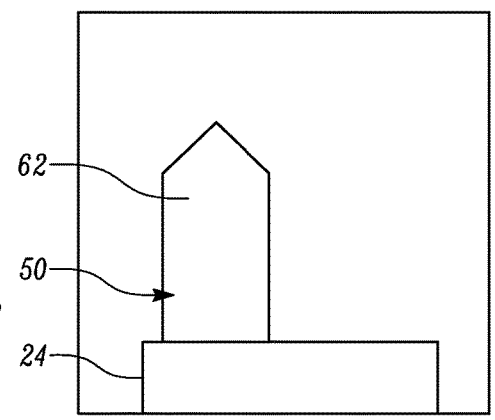
Figure 5A:
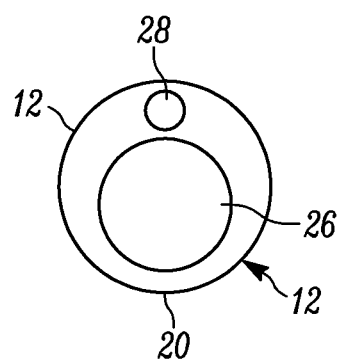
FIGS. 5a through 5d of the drawings are each a cross-sectional view of the feeding tube body of the present disclosure.
Figure 5B:
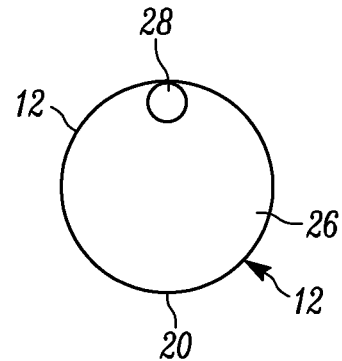
Figure 5C:
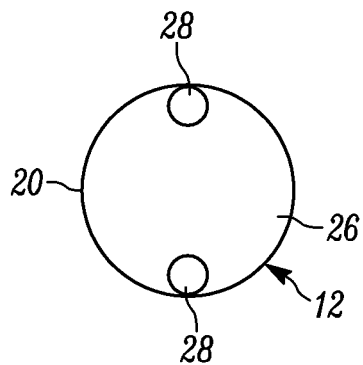
Figure 5D:
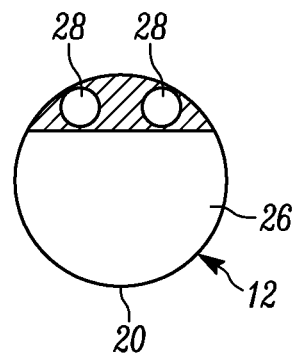
Figure 6A:
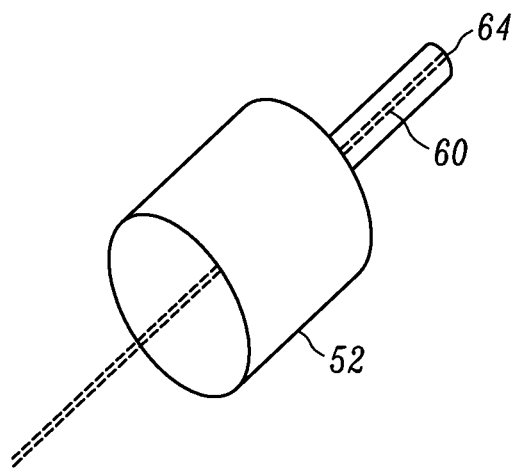
FIGS. 6a and 6b of the drawings are variations of the ferrule connection of the present disclosure.
Figure 6B:
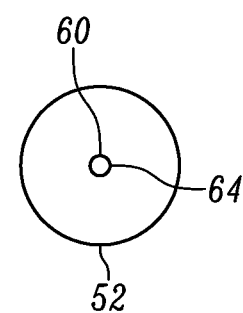

In other configurations, the end dispersion element may comprise a larger fiber optic element 73 (FIG. 3c) extending about the second end of the optical element, and adhered thereto (preferably with an adhesive that is of a higher index of refraction than the optical element). Such a configuration is shown in FIG. 3c, with the entire structure being further encapsulated by a hemispherical epoxy. In other configurations, the epoxy may be omitted. An air gap 75 (FIGS. 3a and 3c) may be presented in many of these configurations between the end dispersion element and the second end of the optical element so as to further aid in dispersion. Two different such configurations are shown in FIGS. 3a and 3c. In still other configurations, the second end of the optical element may be shaped or formed so as to function like an end dispersion element. Such a configuration is shown in FIG. 3b as being further encapsulated by an epoxy hemispherical configuration 71, and also shown in FIG. 3d without any further structures.

In the configuration shown, an intermediate dispersion element 54 is shown in FIG. 1 as comprising an epoxy hemispherical or dome like configuration that extends over the outer surface of the feeding tube body and over the intermediate opening. The formulation of the intermediate dispersion element is the same as, or similar to, the formulation of the end dispersion element. Of course, there may be differences therebetween. That is, where there are multiple different optical lumen, it is contemplated that different lumen may have intermediate openings at different locations, with such different lumen being selectively energized. It is further contemplated that the light may be dispersed from the optical element along substantially the entire length thereof.

Figure 2A:
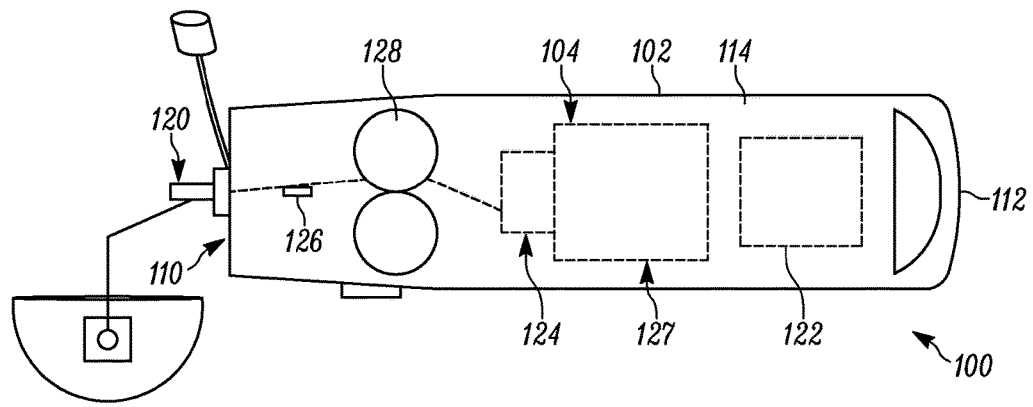
FIG. 2a of the drawings is a top plan view of a light element of the present disclosure.
Figure 2B:
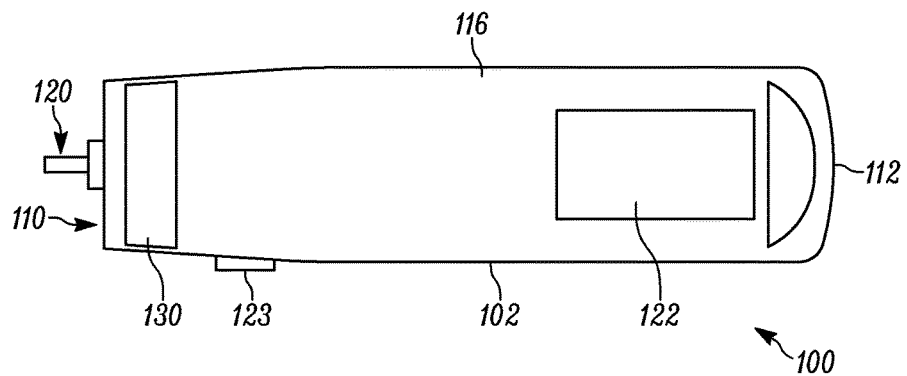
FIG. 2b of the drawings is a bottom plan view of the light element of the present disclosure.

With reference to FIGS. 2a and 2b, the light element 100 is shown as comprising housing 102 and light emitting assembly 104. The housing 102 includes first end 110, second end 112, top surface 114 and bottom surface 116. In the contemplated embodiment, the light element comprises an elongated member which can be grasped by the user in a single hand and operated by the fingers of the user, again with a single hand. A grasping opening 118 may be positioned proximate the second end 112 so as to allow for the coupling to a hook, a chain or ring, or to a carabineer, for example.

The light emitting assembly 104 includes connector 120, power source 122, control circuitry 127 and light source 124. The connector 120 is shown as comprising a fiber optic type connector, of, for example, the type LC, ST, MU or SC. It will be understood that a pigtail connector can be extended between the connector 120 and the tip end 64 of the ferrule connector 52.

The connector is coupled to the light source 124 so that light is directed from the light source to the connector. It will be understood that a number of different configurations are contemplated for the light source. The light source may comprise a light source in the optical spectrum, for example less than approximately 680 nm wavelength. As such, the human eye can be the primary sensor for the light signal through the tissue. In some configurations, a target of approximately 625 to 635 nm wavelength light source is contemplated as it has strikes a balance between depth of tissue penetration and the ability of the human eye (unaided) to detect the signal. At this range, it is approximately 50% brighter for the same power as compared to a light source at approximately 650 nm. It is likewise contemplated that the wavelength may be set or adjustable to accommodate tissue thickness variations and the like. It is contemplated that such a power source comprises an LED. It is further contemplated that in other configurations, an OLED may be utilized.

In another configuration, the light source may comprise a laser light, such as a low level laser device. Among other differences, lasers have lower power requirements, and they have a narrower emitting area, typically. It is contemplated that a laser that is much like a Visual Fault Locator (having higher power class II lasers). The function of the wavelength, irradiance, pulse structure, coherence and polarization are to create trans-lumination of tissue and not a biomodulation effect. A safety switch can be provided which can turn off the device to prevent damage to tissue.

While it is contemplated that visual locating of the light by the eye of the user will be utilized, it is further contemplated that the same may be supplemented by through light sensing devices and the like.

It is further contemplated that the light source can be controlled through control circuitry 127 which is coupled to the power source and to the light source. A plurality of selectors, such as selectors 128 may be provided which direct the control circuitry to perform certain functions relative to the light source, such as pulsing or continuous wavelength transmission, wavelength adjustment and the like. An indicator light 126 may be provided to indicate the status of the device, as well as an on/off switch or pushbutton 123.

It is further contemplated, that an input device 130, such as an optical scanner or RFID scanner may be incorporated so that the device can first identify the patient upon which the device is to be utilized prior to use. It is contemplated that once the patient is scanned, the device may have pre-programmed operation or may default to a predetermined configuration.

In operation, the feeding tube is configured for insertion and placement within the body of the user in a proper position so that necessary nutrients can be sent therethrough. To achieve the same, the light element is first coupled to the feeding tube. That is, through the use of a pigtail fiber optic line, the connector 120 of the light element is coupled to the tip end 64 of the ferrule connector 52. As such, the light source is in communication with the optical element of the optical system of the feeding tube. The light emitting assembly is then activated so as to direct light from the light element to the optical system of the feeding tube assembly.

Once energized, in the configurations that utilize visible light, light can be seen coming from the end dispersion element and any intermediate dispersion elements. The feeding tube assembly is then inserted into the patient, for example, through the mouth (it can be inserted through the nasal passage as well). Upon insertion and movement of the second end through the body, due to the configuration and intensity of the light element, and the configuration of the optical system of the feeding tube assembly, light being emanated from the end dispersion element and any intermediate dispersion elements can be seen through the skin and body of the patient. As a result, the user can see exactly the position of the feeding tube assembly within the body of the user and by correlation of external anatomical landmarks.

Once positioned, the light element can be disconnected from the feeding tube assembly. The feeding tube assembly can be coupled to a feed line so as to direct nutrients through the administration port. It will be understood that, at any time, the light element can be recoupled to the feed tube assembly to determine the current position of the feeding tube assembly. The coupling and decoupling of the feeding tube assembly does not negatively affect the transmission of nutrients through the administration port. The traditional methods of tubing confirmation methods i.e., x-ray, pH, $CO_2$ or aspiration can still be performed with this tubing assembly.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:
1. A feeding tube assembly comprising:
   a feeding tube body having:
      an administration lumen having a proximal opening end and a distal opening; and
      an optical lumen having a proximal end opening and a distal end opening, the optical lumen being isolated relative to the administration lumen, with the distal end opening being adjacent to the distal opening of the administration lumen and with the proximal end opening being spaced apart from the administration lumen;

an optical system having:
an optical element having a first end and a second end, the optical element being positioned within the optical lumen, with the first end corresponding to the proximal end opening, and the second end corresponding to the distal end opening of the optical lumen;
a ferrule connector being positioned proximate the proximal end opening of the optical lumen, spaced apart from the proximal opening of the administration lumen and having a tip end extending from the ferrule connector, with a ferrule surrounding the tip end, the first end of the optical element extending into the tip end, the tip end structurally configured to be attachable to a fiber optic line with the ferrule surrounding the the tip end, with the ferrule connector extending about the feeding tube body to form a ring to encircle the administration lumen and the optical lumen of the feeding tube body; and
an end dispersion element positioned at the second end of the optical element, the end dispersion element structurally configured to disperse light transmitted through the optical element.

2. The feeding tube assembly of claim 1 wherein the feeding tube body defines an elongated substantially cylindrical member, wherein the tip end extends perpendicular to a tangent of the elongated substantially cylindrical member of the feeding tube body.

3. The feeding tube assembly of claim 1 wherein the end dispersion element further comprises a hemispherical member having the second end embedded within the hemispherical member with at least a portion of the feeding tube embedded within the end dispersion member.

4. The feeding tube assembly of claim 3 wherein the hemispherical member has an index of refraction that is greater than an index of refraction of the optical element.

5. The feeding tube assembly of claim 4 wherein the end dispersion element further includes an epoxy with reflectors embedded within the epooxy.

6. The feeding tube assembly of claim 5 wherein the reflectors comprise titanium dioxide particles.

7. The feeding tube assembly of claim 1 wherein the optical element is a first optical element, the end dispersion element further comprises a second optical element encasing the second end of the first optical element, with an air pocket between a portion of the second end of the first optical element and the second optical element, so that the air pocket is also encased by the second optical element.

8. The feeding tube assembly of claim 7 wherein the end dispersion element comprises a hemispherical dispersion element.

9. The feeding tube assembly of claim 1 wherein the second end defines the end dispersion element.

10. The feeding tube assembly of claim 1 further comprising an administration port assembly coupled to the proximal opening end of the administration lumen.

11. The feeding tube assembly of claim 1 further comprising at least one intermediate opening along the optical lumen with the optical element being visible therethrough.

12. The feeding tube assembly of claim 11 further comprising at least one intermediate dispersion element positioned over the at least one intermediate opening.

13. The feeding tube assembly of claim 12 wherein the at least one intermediate dispersion element comprises a hemispherical dispersion element having an index of refraction that is greater than an index of refraction of the optical element.

14. A feeding tube assembly comprising:
a feeding tube body having:
an administration lumen having a proximal opening end and a distal opening; and
an optical lumen having a proximal end opening and a distal end opening, the optical lumen being isolated relative to the administration lumen, with the distal end opening being adjacent to the distal opening of the administration lumen and with the proximal end opening being spaced apart from the administration lumen;
an optical system having:
an optical element having a first end and a second end, the optical element being positioned within the optical lumen, with the first end corresponding to the proximal end opening, and the second end corresponding to the distal end opening of the optical lumen, the first end of the optical element attachable to a fiber optic line, the optical element terminating at a ferrule connector having a tip extending from the ferrule connector with a ferrule extending around the tip end, the ferrule connector extending around the administration lumen and the optical lumen of the feeding tube body; and
an end dispersion element positioned at the second end of the optical element, the end dispersion element structurally configured to disperse light transmitted through the optical element, wherein the second end of the optical element is embedded into the dispersion element, and the dispersion element comprises a hemispherical member that surrounds the second end of the optical element and the distal end of the feeding tube body.

15. The feeding tube assembly of claim 14 further comprising at least one intermediate opening along the optical lumen with the optical element being visible therethrough.

16. The feeding tube assembly of claim 15 further comprising at least one intermediate dispersion element positioned over the at least one intermediate opening.

17. The feeding tube assembly of claim 16 wherein the at least one intermediate dispersion element comprises a hemispherical dispersion element having an index of refraction that is greater than an index of refraction of the optical element.

* * * * *